United States Patent [19]

Broad, Jr.

[11] Patent Number: 5,165,422

[45] Date of Patent: Nov. 24, 1992

[54] APPARATUS FOR ASSEMBLING A CONTRACEPTIVE DEVICE

[76] Inventor: Robert L. Broad, Jr., 2300 Brookwood Dr., SE., Decatur, Ala. 35601

[21] Appl. No.: 614,154

[22] Filed: Nov. 16, 1990

Related U.S. Application Data

[63] Continuation-in-part of Ser. No. 300,139, Jan. 23, 1989, Pat. No. 4,987,905, and a continuation-in-part of Ser. No. 300,140, Jan. 23, 1989, Pat. No. 4,972,850.

[51] Int. Cl.$^5$ ............................................. A61F 6/00
[52] U.S. Cl. .................................. 128/844; 198/803.9; 198/803.1
[58] Field of Search ................... 128/844, 918; 29/235; 206/69; 198/803.3, 803.9, 803.1

[56] References Cited

U.S. PATENT DOCUMENTS

| 952,256 | 3/1910 | Jacobsen | 198/803.9 X |
|---|---|---|---|
| 3,992,766 | 11/1976 | Field | 29/235 |
| 4,149,623 | 4/1979 | Nelson | 198/803.9 X |
| 4,488,637 | 12/1984 | Loeffler | 198/803.9 |
| 4,607,474 | 8/1986 | Jarvis | 29/235 X |
| 4,731,064 | 3/1988 | Heyden | 604/352 |
| 4,872,463 | 10/1989 | Nishizōno | 128/844 |
| 4,905,986 | 3/1990 | Müller | 198/803.9 X |
| 4,979,349 | 12/1990 | Focke | 198/803.9 X |
| 4,982,834 | 1/1991 | Jacobsen | 198/803.9 X |
| 4,984,680 | 1/1991 | Hamano | 198/803.9 |

FOREIGN PATENT DOCUMENTS

| 111720 | 12/1928 | European Pat. Off. | 604/349 |
|---|---|---|---|
| 2410697 | 6/1974 | Fed. Rep. of Germany . | |
| 617611 | 7/1978 | U.S.S.R. | 198/803.9 |
| 1601592 | 11/1981 | United Kingdom | 198/803.9 |

Primary Examiner—Robert A. Hafer
Assistant Examiner—Sam Rimell

[57] ABSTRACT

In an apparatus for assembling a contraceptive device, an apparatus for transferring a condom from a conveyor to a moving packaging strip, the condom having on opposite sides thereof a pair of polymeric strips, each of the strips having one end thereof rolled into the condom and the other end thereof depending from the condom, wherein a hand having a plurality of fingers which engage and hold the rolled condom carries the condom from a position above the conveyor to a position above the packaging strip. As the hand is lowered to deposit the condom on the packaging strip a pair of sweeps sweep the depending ends of the polymeric strips to generally horizontal positions such that when the condom is deposited on the packaging strip the polymeric strips will be free of wrinkles and folds.

8 Claims, 5 Drawing Sheets

APPARATUS FOR ASSEMBLING A CONTRACEPTIVE DEVICE

This application is a continuation-in-part application of application Ser. No.: 07/300,139 filed Jan. 23, 1989 for "NO HANDS CONTRACEPTIVE DEVICE" Now U.S. Pat. No. 4,987,905 and application Ser. No.: 07/300,140 filed Jan. 23, 1989 for "NO HANDS CONTRACEPTIVE DEVICE" Now U.S. Pat. No. 4,972,850

BACKGROUND

1. Field of the Invention

This invention relates to apparatus for assembling contraceptive devices.

2. Prior Art

Conventional condoms, after being suitably tested, are fed onto a moving lower strip which will become the bottom portion of the package that encloses and protects the condom. With the condoms preceisely spaced on the moving lower strip, an upper strip is fed downward in alignment with the lower strip, the strips being heat-sealable to each other. The strips are then heat-sealed to each other around the condom to form the finished package. The strips are then cut to separate the packaged condoms.

SUMMARY OF THE INVENTION

In an apparatus for assembling a contraceptive device including a condom having a pair of polymeric strips rolled into opposite sides thereof with the strips having free ends depending from the condom on opposite sides thereof, a "hand" moveable from a position above a conveyor to a position above a moving lower packaging strip carries fingers which close on the rolled condom to carry the condom into position above the packaging strip. The apparatus is provided with a pair of sweeps each being moveable from a position below the condom and between the depending strips to a position such that the free ends of the strips are moved outward to extend in generally horizontal directions from the condom prior to depositing the condom on the packaging strip. The movement of the sweeps is timed to hold the polymeric strips in this horizontal position as the hand is lowered to place the condom on the packaging strip, so that the polymeric strips will extend transversely across the packaging strip without folds or wrinkles. An upper packaging strip is then heat-sealed to the lower packaging strip to enclose the condom.

DETAILED DESCRIPTION OF THE INVENTION

The prior art described above works well for conventional condoms but when it is desired to package the contraceptive device disclosed in the co-pending application referenced above, this conventional procedure cannot be used. These co-pending applications disclose and claim a contraceptive device made up of a condom having a pair of polymeric strips rolled into the condom on opposite sides thereof and having free ends extending from the rolled portion of the condom. When the device is enclosed between heat-sealable packaging strips to form a package, the free ends of the strips will be secured to the package at opposite sides thereof.

For packaging this contraceptive device, the polymeric strips cannot extend along the heat-sealable packaging strips but must extend transversely across these strips to the edges thereof. Also, the polymeric strips must be free of wrinkles and folds to insure that after the packaging strips have been heat-sealed together, no air can enter the package. If there is even the slightest fold or wrinkle in the polymeric strips in that area of the packaging strips which is to be heat-sealed, the package will likely not be hermetically sealed and ozone from the atmosphere may enter the package and damage the condom.

Figures 1, 2:
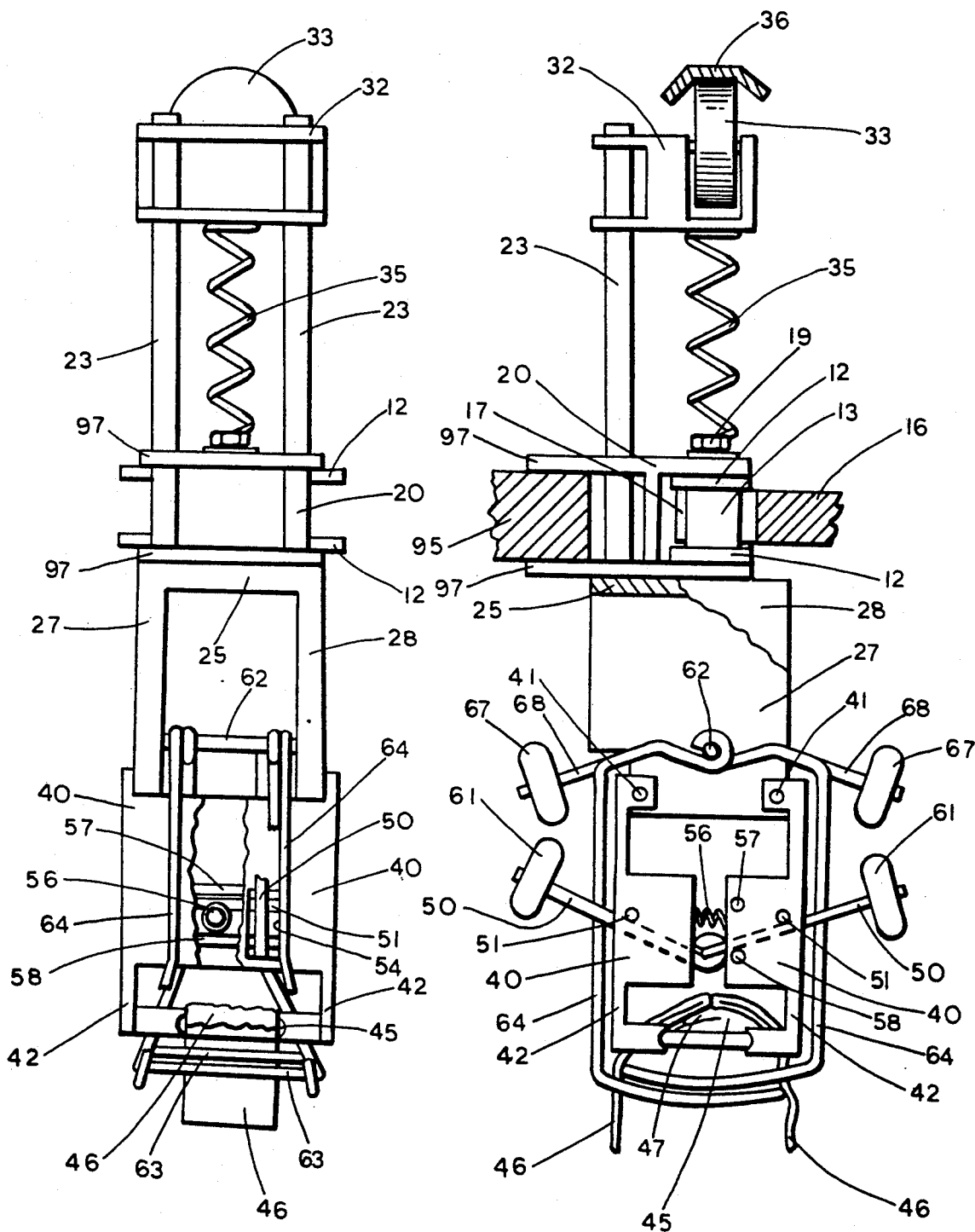
FIG. 1 is a front view of the apparatus of this invention showing the manner in which the apparatus holds a condom for transfer from one conveyor to another.
FIG. 2 is a side view of the apparatus shown in FIG. 1.
Figure 3:
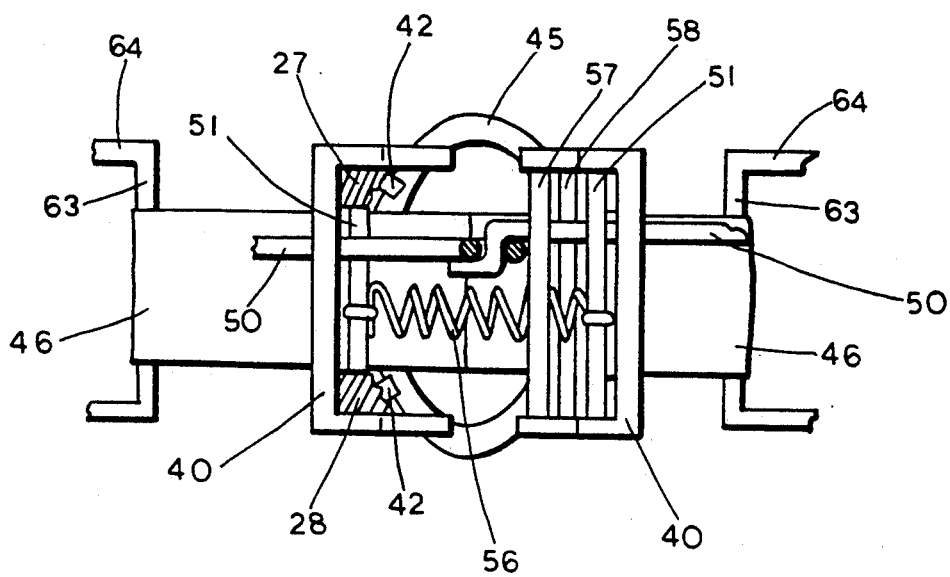
FIG. 3 is a sectional view taken along line 3—3 of FIG. 5 showing the elements which effect the opening and closing of the fingers which hold the condom.

Referring now in detail to the drawings, there is shown in FIGS. 1 and 2 a roller chain made up of links 12 and rollers 13, the chain being supported and driven by a sprocket 16 having teeth 17 (FIG. 1). The sprocket 16 is supported by a frame or base 18 (FIGS. 5 and 6) which supports the apparatus disclosed herein. Secured to the chain by a set screw 19 is a first bracket 20 which serves as a support for the remainder of the apparatus.

A pair of guide rods 23 extend through holes in the first bracket 20 and have the lower ends thereof secured to a support element 25 having a pair of spaced, depending flanges 27 and 28, the guide rods 23 being slidably mounted in the holes in the first bracket so that the support element 25 can be lowered relative to the first bracket 20 and the chain.

The upper ends of the guide rods 23 are secured to a second bracket 32 which is provided with a cam or track-following roller 33. A compression spring 35 positioned between the first and second brackets serves to urge the guide rods 23 and the support element 25 in an upward direction. A stationary cam or track 36 (FIG. 1) mounted on the base 18 and positioned above the path of the roller 33 serves to engage the roller 33 and compress the spring 35 to lower the support element 25 at the desired locations.

A pair of holding elements 40 pivotally attached to the flanges 27 and 28 by pins 41 are each provided with a pair of depending fingers 42, with each pair of fingers 42 being positioned to engage a rolled condom 45 at points on opposite sides of a pair of polymeric strips 46 which are rolled into the condom on opposite sides thereof. The fingers 42 hold the condom for transfer from one conveyor to another, with FIG. 5 best showing the positioning of the fingers relative to the condom. The strips 46 have free ends which extend from the rolled condom 45 and depend from the condom on opposite sides thereof. The purpose of the strips is to unroll the condom onto the user's penis when the strips are pulled.

Preferably, the strips 46 have widths such that the sums of the widths of the two strips is at least 20% of the length of the circumference of the rolled condom. More preferably, the strips 46 have a width which is great enough to cause the rolled condom 45 to assume an elliptical configuration having a length to width ratio of a least 1.2. This is discussed in greater detail in the referenced co-pending applications, those portions of such applications being incorporated here by reference.

The fingers 42 are opened and closed by a toggle mechanism made up of a pair of levers 50 which may be made of heavy wire and which are secured to a pair of rods 51 pivotally mounted on the holding elements 40. The inner ends of the levers 50 are pivotally attached to each other between the holding elements 40, with the outer ends of the levers extending through slots 54 (FIG. 5) in the holding elements 40. A tension spring 56 connected between the rods 51 serves to pull the holding elements 40 toward each other to close the fingers 42, with each of the fingers 42 having a recess or groove 55 for receiving the edge of the rolled portion of the condom.

Figure 4:
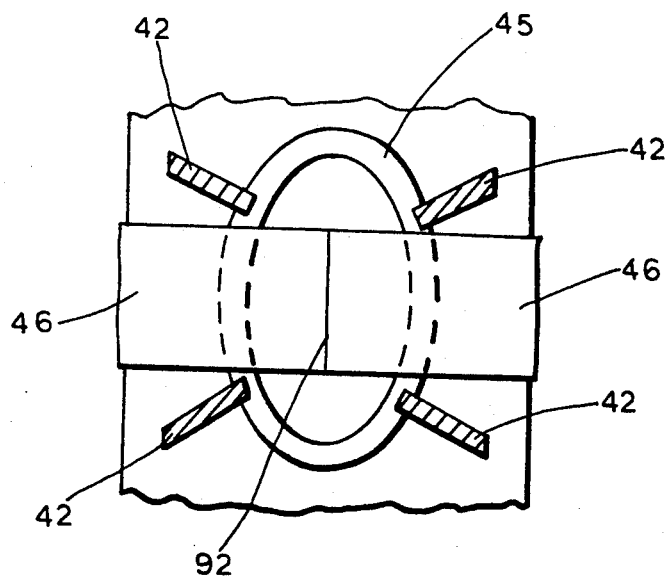
FIG. 4 is a sectional view taken on line 4—4 of FIG. 5 showing the positioning of the fingers holding the condom.

A pair of stop rods 57 and 58 attached to one of the holding elements 40 serves to limit the movement of the levers 50 to limit the opening and closing of the fingers 42. When the levers 50 are stopped by engagement with the stop rod 57, the pairs of fingers 42 are held in an open position to free the condom as best shown in FIG. 4. When the levers 50 are stopped by engagement with the stop rod 58, the fingers 42 are in a closed position to hold the condom 45.

Pairs of stationary cams or tracks 60 (FIG. 6) mounted on the base 18 serve to engage rollers 61 on the levers 50 to move the levers up and down to operate the toggle mechanism to open and close the fingers 42 as the device is carried past the cams 60 by the chain. It is understood that some of the pairs of cams 60 will be above the rollers 61 while others will be below, so that the rollers 61 can be moved in both up and down directions to open and close the fingers 42.

It is not essential that the stop rods 57 and 58 be used. The lengths of the slots 54 can be selected in such a manner that the engagement of the levers 50 with the ends of the slots 54 will stop the levers 50 at the proper places to hold the fingers 42 in open and closed positions.

Figure 8:
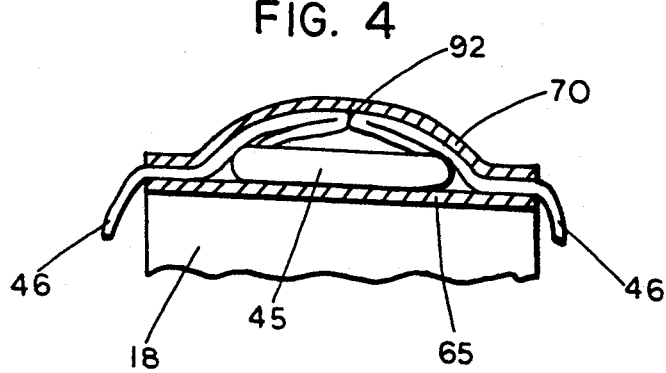
FIG. 8 is a cross sectional view of the packaged condom.
Figure 5:
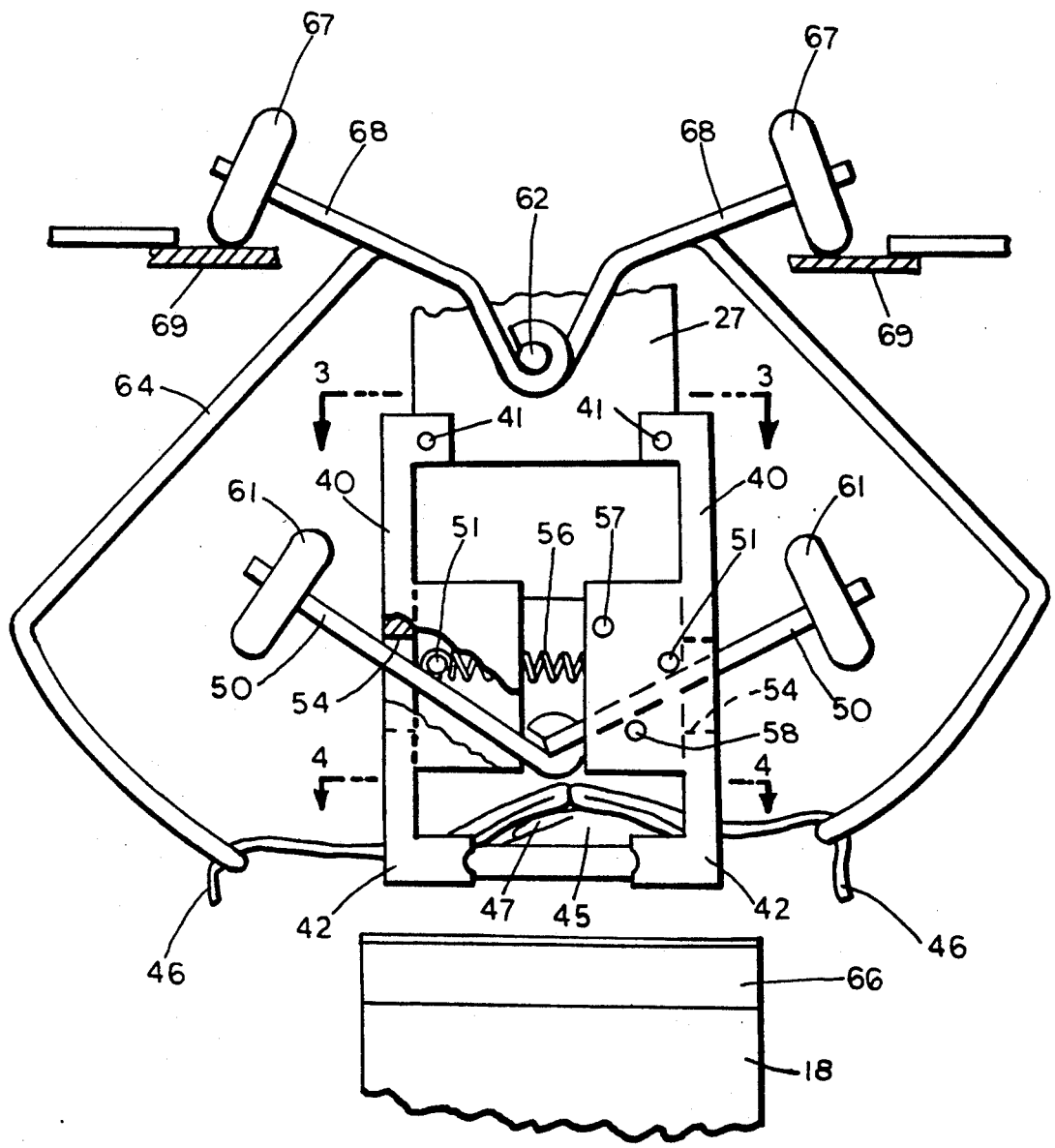
FIG. 5 is an enlarged fragmentary view showing the manner in which the sweeps move the free ends of the depending polymeric strips outward from the condom in a generally horizontal direction prior to the condom being deposited on a strip which is to be part of the package for the condom.
Figure 6:
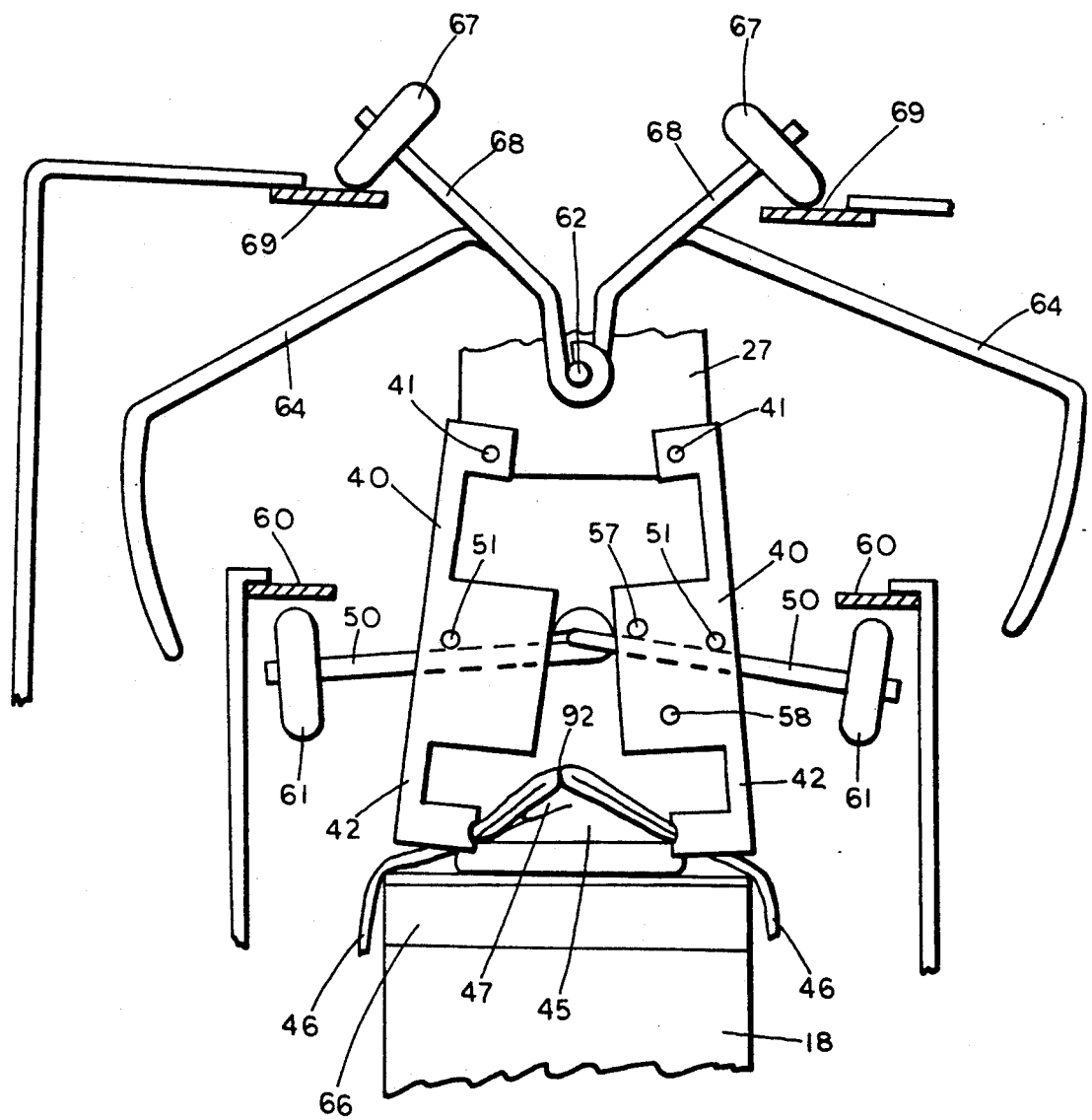
FIG. 6 is a fragmentary view showing the apparatus of FIG. 5 after the fingers have opened to deposit the condom on the strip.
Figure 7:
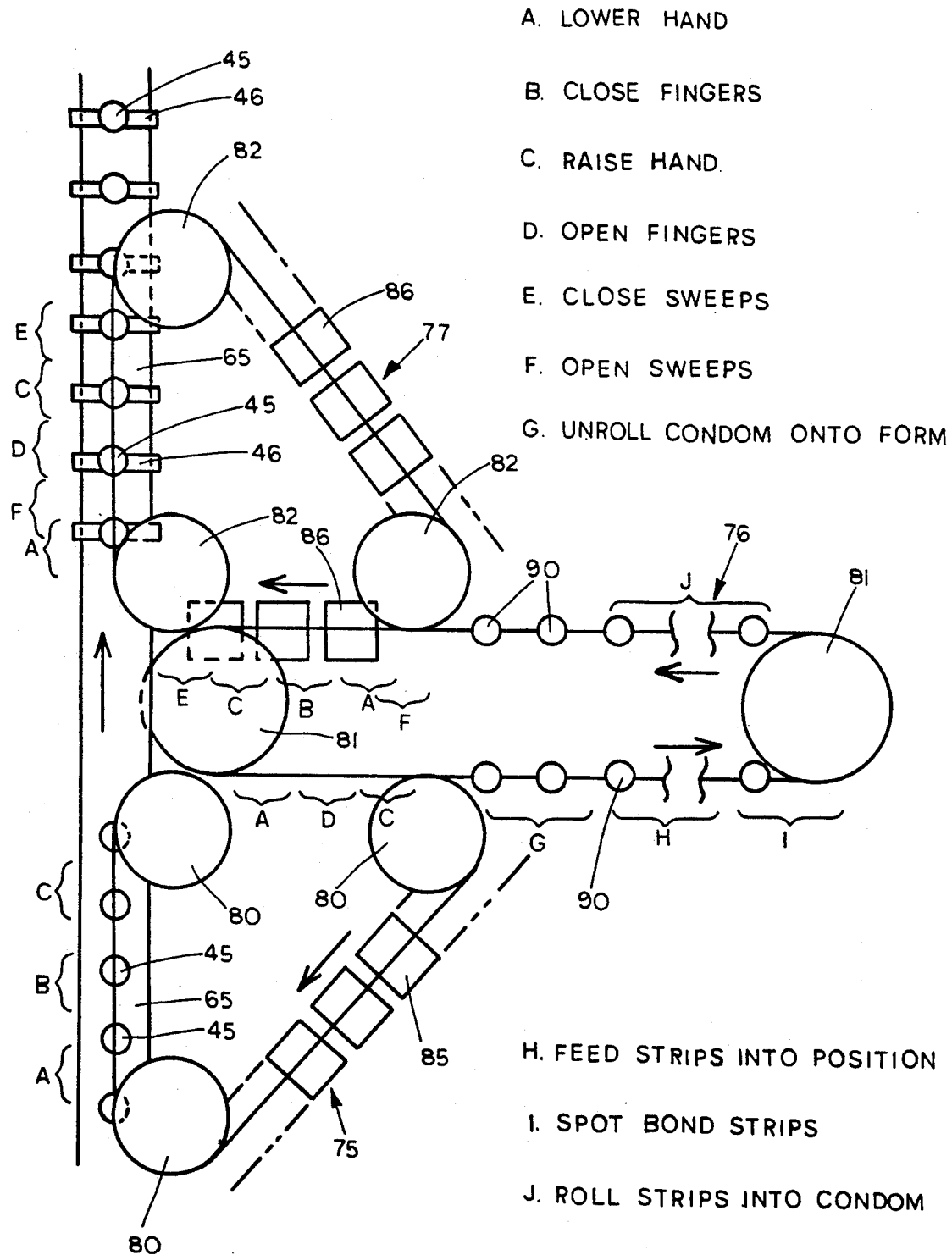
FIG. 7 is a schematic view showing the apparatus with which the apparatus of this invention is used.

The condom 45 is to be transferred to a lower heat-sealable, packaging strip 65 which may be carried by a conveyor 66 or simply pulled along the base 18, as best shown in FIGS. 5-7. The strip 65 will be the bottom part of a package which will enclose the condom 45 in the finished product. An upper, heat-sealable packaging strip 70 (FIG. 8) forms the top part of the package, with (in the finished product) the packaging strips being sealed to each other around the edges of the package by the application of heat and pressure. This type of sealing is known.

When the condom 45 is placed on the lower strip 65, it is essential that the polymeric strips 46 be free of wrinkles and folds. Even a small wrinkle or fold in the strips may prevent the package from being hermetically sealed when the heat-sealing operation is carried out, thereby allowing ozone from the atmosphere to enter the package and damage the condom.

The apparatus disclosed and claimed herein will place the condom 45 on the strip 65 with the polymeric strips 46 extending transversely across the strip 65 to the edges thereof without any folds or wrinkles.

The apparatus is provided with a pair of elements 64 pivotally mounted on a rod 62 attached to the flanges 27 and 28 and having generally horizontal portions 63 (FIG. 2) which engage the polymeric strips 46 to "sweep" these strips from the depending positions shown in FIG. 1 to the generally horizontal positions shown in FIGS. 5 and 6. In the legend in FIG. 7 and hereafter in this specification the elements 64 are referred to as "sweeps".

Rollers 67 mounted on rods 68 attached to the sweeps 64 engage cams or tracks 69 (FIGS. 5 and 6) mounted on the base 18 to raise the rollers and move the sweeps 64 from the closed position shown in FIG. 1 to the open position shown in FIGS. 5 and 6. The cams 69 are simply flat strips which are curved or bent to move the rollers 67 up to open the sweeps.

FIG. 7 schematically shows the structure in which the above-described apparatus is used. This structure includes first, second and third conveyors, 75, 76 and 77, respectively, of the roller chain type mounted on and driven by sets of sprockets 80, 81 and 82, respectively. The first and third conveyors 75 and 77 carry the devices described above, with these devices being spaced on the conveyors 75 and 77 a distance equal to the length of the package in which the condom will be sealed. In FIG. 7 these devices are shown schematically as boxes 85 and 86, respectively, and are referred to as "hands" since the devices, with the fingers 42, resemble a hand and fingers in function. This analogy will make it easier to follow the sequence of operations of the structure shown in FIG. 7.

The conveyor 75 follows a path which defines a right triangle, with one of the triangle legs being positioned in alignment with and above the moving strip 65 which carries the spaced condoms 45. The other leg of the triangle is aligned with and positioned above the conveyor 76. The conveyors 75, 76 and 77 travel at the same linear speed as the strip 65, so that the hands 85 and 86 on the conveyors 75 and 77 travel at the same speed as the condoms 45 on the strip 65. The hands 85 and 86 are also so positioned that one of the hands is directly above each condom to be transferred from one conveyor to another, with no relative horizontal movement between the moving hand and the moving condom.

Letters A through J in FIG. 7 indicate the sequence of operation of the apparatus shown in FIG. 7. For example, when a rolled condom 45 on the moving strip 65 moves into position beneath the conveyor 75, it will be directly below one of the hands 85 with the fingers 42 in an open position. The track 36 will move the hand 85 downward until the condom 45 on the strip 65 is between the fingers 42, whereupon the cams 60 will operate the toggle mechanism to close the fingers 42 on the condom. At this point, the track 36 will curve upwardly to allow the spring 35 to raise the hand 85 and lift the condom off the strip 65.

The sweeps described above are not needed or used on the hands 85 on the conveyor 75, since the strips 46 are not rolled into the condoms at this point.

The conveyor 75 then carries the condom 45 into position above the conveyor 76, the conveyor 76 being provided with forms 90 onto which the condom will be unrolled. The forms 90 extend vertically upward from the conveyor 76 and have a generally cylindrical configuration with rounded upper ends to conform to the shape of the unrolled condom 45. These forms have the same spacing as the hands on the conveyors 75 and 77.

The conveyor 76 is lower than the conveyors 75 and 77, such that the tops of the forms 90 are generally in the plane of the condom 45 when the fingers 42 holding the condom are in their lowermost position.

The letters A, D and C next to the conveyor 76 indicate that the hand 85 is lowered to deposit the rolled condom 45 on the end of one of the forms 90, whereupon the fingers 42 are opened and the hand 85 raised to leave the rolled condom on the form 90. At station G the condom is unrolled onto the form 90. This may be done by the use of rotating brushes or rollers (not shown).

At station H the polymeric strips 46 will be fed downwardly on opposite sides of the condom 45 and brought into contact with the condom by an appropriate strip feeding apparatus (not shown). A small amount of lubricant suitable for use with condoms may be used to cause the strips 46 to adhere to the condom 45 on the form 90 after the strip feeding apparatus is withdrawn. This apparatus for feeding the strips into this position is not a part of this invention.

Before the strip feeding apparatus releases the strips 45 these strips are brought together above the condom 45 on the form 90 and are spot-bonded together. By "spot-bonded" it is meant that the strips 46 are secured to each other in a bond which has sufficient strength to hold the strips together after the strip feeding apparatus is withdrawn but which is weaker than the strip itself. With such a bond, when sufficient tension is applied to the ends of the strips the bond will break and allow the strips 46 to separate before sufficient tension is applied to break one of the strips 46. The bonded area is indicated by reference numeral 92.

The purpose of the spot-bonding is to provide sufficient slack in the strips 46 that the package can be torn into two parts and the two parts of the package moved apart to pull the condom out of the package without prematurely unrolling the condom. If the condom unrolls even a small amount prematurely, it is likely to become so tangled that it cannot be used. This problem is described in detail in the co-pending applications identified above.

The spot-bonding is preferably done by fusing portions of the polymeric strips 46 together by the use of heat. For example, the spot-bonding may be achieved by holding the strips 46 in contact with each other and piercing them with a heated pin to fuse them together. Touching the strips with the tip of a hot soldering gun while the strips are held in contact with each other melts a hole of $\frac{1}{8}$ inch diameter in the strips 46 and leaves them fused together around the periphery of the hole. The spot-bonding can also be done by applying a drop of an adhesive to one of the strips and then bringing them into contact with each other.

Most condoms have a reservoir end, indicated by the reference numeral 47 in FIGS. 1, 5 and 6. It is preferred that this reservoir end be collapsed or flattened against the end of the form 90 before the spot-bonding operation. This removes air from the reservoir and allows the spot-bonding to be done nearer the main body of the condom. This can be done by providing the form 90 with a passageway (not shown) extending from a point near the base of the form to and through the end of the form under the reservoir. By applying a slight vacuum to this passageway at the base of the form to pull air from the passageway and the interior of the reservoir end, atmospheric pressure will collapse or flatten the reservoir end 47 against the end of the form. The spot-bonding operation is then carried out.

At station J the strips 46 and the condom 45 are rolled so that the completely rolled condom leaves the station J sitting atop the form 90. This rolling may be done by the use of rollers or brushes (not shown). This apparatus is not a part of this invention.

Some brands of condoms are easier to roll than others. The use of the strips 46 will cause almost any brand of condom to be slightly more difficult to roll on the form 90, with the difficulty increasing as strip width is increased. If a given condom is difficult to roll, it will tend to slide along the form 90 and develop an accordion-like fold rather than rolling. This, of course, is unacceptable.

One way to avoid this problem is to increase the diameter of the form 90 so that the condom 45 is stretched in a circumferential direction when it is unrolled onto the form 90 at the station G. This circumferential stretch should be at least 5% and is preferably at least 10%, i.e., stretched to a circumference of 110% of the circumference of the unstretched condom. Also, it is preferred that the form 90 be convered with a material which has a high static coefficient of friction with the material of the condom, such as rubber.

As the circumferential stretch of the condom 45 is increased, the likelihood that the condom will pop upward from the end of the form 90 as rolling is completed is increased. If the condom does not remain on the top of the form 90 it cannot be picked up by the conveyor 77. Thus, it may be desirable or necessary in some cases to provide some sort of structure (not shown) above the form 90 to retain the rolled condom 45 on the form after rolling is completed.

After the condom is rolled at station J, it is carried by the conveyor 76 under one leg of the conveyor 77, where it passes stations F, A, B, C and E in that order. At the station F the sweeps 64 are opened to the position shown in FIG. 6 so that the lower ends of the sweeps will not engage the form 90. The hand 86 is then lowered (station A) and the fingers 42 are closed (station B) to hold the condom 45, whereupon the hand 86 is raised (station C) and the sweeps 64 released (station E) to fall back to the positions shown in FIG. 1.

The condom 45, with the strips 46 depending therefrom as shown in FIG. 1 is carried to a point where it is above the packaging strip 65 and the track 36 begins to move the hand 86 downward (station A). Just before the condom 45 touches the strip 65, the sweeps 64 are opened (station F) from the position shown in FIG. 1 to the position shown in FIG. 5. This sweeps the polymeric strips 46 outward to positions where the strips extend outward from the condom in generally horizontal directions. The track 36 then moves the hand 86 downward until the condom 45 is resting on the packaging strip 65. (Notice the overlap of stations A and F.)

With the fingers 42 still holding the condom 45 on the strip 65, the sweeps 64 are opened to the positions shown in FIG. 6 to completely free the strips 46 and allow them to fall onto the packaging strip 65 free of wrinkles and folds. The fingers 42 are then opened (station D) and the hand 86 is raised (station C). After the hand 86 is raised, the rollers 67 clear the cams 69 to allow the sweeps 64 to fall back to a closed position (station E).

Since the conveyors 75, 76 and 77 and the strip 65 all travel at the same speed, the condoms 45 will be deposited on the strip 65 with the same spacing they had before being picked up by the conveyor 75.

After the condom 45 has cleared the conveyor 77 the upper packaging strip 70 is fed downward to cover the condom and the lower strip 65. The packaging strips are then sealed around the edges by the application of heat and pressure to complete the condom package. At a subsequent station (not shown) any portions of the strips 46 which extend beyond the edges of the package are severed.

It may be necessary or desirable to stabilize the hands 85 and 86 on the moving conveyors 75 and 77 to insure that the condom will be placed at the desired position on the form 90 and then later on the moving strip 65. To insure lateral stability, i.e., keep the fingers 42 from moving laterally from the desired path during the pickup of depositing of the condom, the track 36 (FIG. 1) has the configuration of an inverted through to prevent lateral movement of the roller 33. This restricts lateral movement of the fingers 42.

Stability in the direction of movement of the hands 85 and 86 is achieved by the use of an elongated horizontal bar 95 (FIG. 1) made of a low friction material such as polytetrafluoroethylene or nylon and mounted on the base 18. The bar 95 should have a tapered leading end (not shown) such that it will easily enter the space between a pair of flanges 97 on the moving bracket 20. The bar 95 engages the flanges 97 to prevent any rocking movement of the fingers 42 relative to the bracket 20 in the direction in which the conveyor is traveling.

For convenience, both the bar 95 and the sprocket 16 are shown in FIG. 1. However, it should be understood that several of the bars 95 are used and each will be located not adjacent to a sprocket as shown but at a location where a condom is being picked up or deposited by the fingers 42. The use of the bars 96 and the trough-like track 36 insures that the fingers 42 deposit the condom 45 at precisely the desired operation.

The exact positioning of the rollers 61 is not shown in the drawings. However, it should be understood that the rollers 61 are so positioned and are of such a size that the sweeps 64 can be opened and closed without engaging the rollers 61.

What is claimed is:

1. Apparatus for transferring a rolled condom from a conveyor to a moving packaging strip, said condom having on opposite sides thereof a pair of strips each having one end rolled into the condom and the other end thereof depending from the rolled condom, comprising
   a. a base,
   b. means for holding the rolled condom in a generally horizontal position with said other ends of said strips depending from the condom on opposite sides thereof,
   c. means on the base for carrying the holding means from a position above the conveyor to a position above the packaging strip,
   d. a pair of sweeps, moveably mounting on the holding means, said sweeps each having a portion which is moveable outward from a position below the rolled condom and between the depending strips to a position generally horizontally spaced from the condom to sweep the depending ends of the strips to such generally horizontal positions so that when the holding means deposits the condom on the packaging strip said pair of strips will extend transversely past the edges of the packaging strip and be free of wrinkles and folds, and
   e. means associated with the sweeps for moving said sweeps to move said portions from said positions below the condom to said generally horizontally spaced positions.

2. The apparatus of claim 1 wherein said holding means is mounted on the carrying means for movement between upper and lower positions with means mounted on the base for moving the holding means to said lower position at the location where the condom is to be picked up from the conveyor and at the location where the condom is to be deposited on the packaging strip.

3. The apparatus of claim 1 wherein the sweeps are operated by a plurality of stationary cams mounted on the base.

4. Apparatus for transferring a rolled condom from a conveyor to a moving packaging strip, said condom having on opposite sides thereof a pair of strips each having one end rolled into the condom and the other end thereof depending from said condom, comprising
   a. a base,
   b. a support element,
   c. means on the base for supporting and carrying the support element from a position above the conveyor to a position above the packaging strip,
   d. a pair of holding elements moveably mounted on the support element, each of said holding elements having a pair of spaced fingers extending downward to engage the condom on opposite sides thereof, said holding elements being moveable to move the fingers toward each other to engage and hold the rolled condom and to move the pairs of fingers away from each other to release the condom,
   e. means connected to the holding elements for moving the pairs of fingers toward and away from each other,
   f. a pair of sweeps mounted on the support element, said sweeps having generally horizontal portions, said sweeps being moveably mounted to carry said horizontal portions from positions below the condom and between the depending strips to positions generally horizontally spaced from the condom to sweep said depending strips to positions extending generally horizontally from said condom, and
   g. means associated with the sweeps for moving said sweeps.

5. The apparatus of claim 4 wherein a spring connected between the holding elements urges the pairs of fingers toward each other to a closed position to hold the condom.

6. The apparatus of claim 4 wherein the sweeps are each provided with a cam follower and the base is provided with a stationary cam positioned to be engaged by the cam follower for opening the sweeps.

7. The apparatus of claim 6 wherein the cam followers are rollers and the cams are tracks mounted above the base.

8. The apparatus of claim 7 wherein the sweeps are pivotally attached to the support element.

* * * * *